(12) United States Patent
Mamedov et al.

(10) Patent No.: US 8,288,446 B2
(45) Date of Patent: Oct. 16, 2012

(54) CATALYTIC HYDROGENATION OF CARBON DIOXIDE INTO SYNGAS MIXTURE

(75) Inventors: Agaddin M. Kh. Mamedov, Stafford, TX (US); Abdulaziz M. Al-Jodai, Riyadh (SA)

(73) Assignee: Saudi Basic Industries Corporation, Riyadh (SA)

(*) Notice: Subject to any disclaimer, the term of this patent is extended or adjusted under 35 U.S.C. 154(b) by 419 days.

(21) Appl. No.: 12/452,189

(22) PCT Filed: Jun. 24, 2008

(86) PCT No.: PCT/EP2008/005069
§ 371 (c)(1),
(2), (4) Date: Dec. 18, 2009

(87) PCT Pub. No.: WO2009/000494
PCT Pub. Date: Dec. 31, 2008

(65) Prior Publication Data
US 2010/0105962 A1    Apr. 29, 2010

(30) Foreign Application Priority Data
Jun. 25, 2007  (EP) .................................. 07075510

(51) Int. Cl.
*C07C 27/00* (2006.01)
*C01B 3/26* (2006.01)
(52) U.S. Cl. ......................... 518/700; 518/702; 423/651
(58) Field of Classification Search .................. 518/700, 518/702; 423/651
See application file for complete search history.

(56) References Cited

U.S. PATENT DOCUMENTS

| | | | |
|---|---|---|---|
| 1,913,364 | A | 6/1933 | Bader et al. |
| 6,833,013 | B1 | 12/2004 | Sanfilippo et al. |
| 2003/0113244 | A1 | 6/2003 | Dupont et al. |
| 2007/0142482 | A1 | 6/2007 | Jung et al. |

FOREIGN PATENT DOCUMENTS

| | | |
|---|---|---|
| GB | 2 168 718 A | 6/1986 |
| GB | 2 279 583 A | 1/1995 |
| WO | WO 96/06064 | 2/1996 |

OTHER PUBLICATIONS

D.Shuang et al., "Oxidative Dehydrogenation of Ethane with Carbon Dioxide to Ethylene over Nanosized Cr2O3 Catalysts", Chinese Journal of Catalysis, vol. 24, No. 10, pp. 744-750 (Oct. 2003).
International Search Report; International Application No. PCT/EP2008/005069; International Filing Date Jun. 24, 2008; Date of Mailing Jul. 7, 2009, 4 pages.
Written Opinion of the International Searching Authority; International Application No. PCT/EP2008/005069; International Filing Date Jun. 24, 2008; Date of Mailing Jul. 7, 2009; 6 pages.
Ailing Sun et al., "Ethylenebenzene Dehydrogenation in the Presence of Carbon Dioxide over Alumina Supported Catalysts" Catalysis Today, pp. 273-279 (2004).
T. Badstube et al., "Screening of Catalysts in the Oxidative Dehydrogention of Ethylbenzene with Carbon Dioxide", Applied Catalysis A: General , vol. 204, pp. 153-165 (2000).
Yoshihiro Sakurai et al., "Dehydrogenation of Ethylbenzene with an Activated Carbon-Supported Vanadium Catalyst", Applied Catalysis A: General, vol. 192, pp. 281-288 (2000).
Howard F. Rase, "Handbook of Commercial Catalysts", pp. 405-407 (1998).
Ye et al.;Effect of Modifiers on the Activity of a Cr2O3/Al2O3 Catalyst in the Dehydrogenation of Ethylbenzene with CO2 Green Chemistry; 2005, pp. 524-528; Royal So of Chem.

*Primary Examiner* — Jafar Parsa
(74) *Attorney, Agent, or Firm* — Cantor Colburn LLP

(57) ABSTRACT

The invention relates to a process of making a syngas mixture containing hydrogen, carbon monoxide and carbon dioxide, comprising a step of contacting a gaseous feed mixture containing carbon dioxide and hydrogen with a catalyst, wherein the catalyst substantially consists of chromia/alumina. This process enables hydrogenation of carbon dioxide into carbon monoxide with high selectivity, and good catalyst stability over time and under variations in processing conditions.

The process can be applied separately, but can also be combined with other processes, for example up-stream with other synthesis processes for making products like aliphatic oxygenates, olefins or aromatics.

10 Claims, No Drawings

CATALYTIC HYDROGENATION OF CARBON DIOXIDE INTO SYNGAS MIXTURE

The invention relates to a catalytic process for producing a syngas mixture from carbon dioxide, more specifically to a process of making a syngas mixture containing hydrogen, carbon monoxide and carbon dioxide, comprising a step of contacting a gaseous feed mixture containing carbon dioxide and hydrogen with a chromium-containing catalyst.

Such a process is known from patent application US 2003/0113244 A1. This publication discloses a process for the production of a syngas (generally used abbreviation for synthesis gas) mixture that is rich in carbon monoxide, by converting in the gas phase at 1-4 MPa and at a temperature between 300 and 520° C., $CO_2$ and $H_2$ in the presence of a catalyst based on zinc oxide and chromium oxide, and not containing iron. The simultaneous presence of Zn and Cr is stressed to be essential for a good reaction rate, whereas presence of Fe (and Ni) should be avoided to suppress forming of methane via so-called methanation side-reactions. Formation of methane as a by-product is generally not desired, because it not only means less CO is being produced, but also because the accompanied formation and deposition of coke will reduce catalyst life-time.

In the past decades, numerous processes have been developed to produce synthesis gas, which is one of the most important feedstocks in the chemical industry. Syngas is a gaseous mixture containing hydrogen ($H_2$) and carbon monoxide (CO), which may further contain other gas components like carbon dioxide ($CO_2$), water ($H_2O$), methane ($CH_4$), and/or nitrogen ($N_2$). Natural gas and (light) hydrocarbons are the predominant starting material for making synthesis gas. Syngas is successfully used as synthetic fuel and also in a number of chemical processes, such as synthesis of methanol or ammonia, Fischer-Tropsch type and other olefin syntheses, hydroformulation or carbonylation reactions, reduction of iron oxides in steel production, etc.

Such syngas processes frequently use methane as a main feed gas component, which can be converted to syngas by steam reforming, partial oxidation, $CO_2$ reforming, or by a so-called auto-thermal reforming reaction. One of the disadvantages associated with syngas production by steam reforming of methane, which is the most widely applied process to produce syngas, is that the composition of the produced gas mixture is limited by the reaction stoichiometry to $H_2$/CO ratios of 3 or higher. In order to avoid such drawback, and initiated as well by the strong influence that an increasing amount of $CO_2$ in the atmosphere has on the environment, research has been conducted to manufacture syngas from carbon dioxide as a raw material; based on the known equilibrium reaction (generally referred to as the water gas shift (WGS) or more specifically, as in the present case, the reverse water gas shift (RWGS) reaction):

$$CO_2 + H_2 \leftrightarrows CO + H_2O$$

In e.g. GB 2168718 A it was proposed to combine the RWGS reaction with steam reforming of methane. Such combination of reactions, for example by mixing the respective product streams, allows to adjust the molar ratio of hydrogen to carbon monoxide ($H_2$/CO), or better the stoichiometric number $SN=([H_2]-[CO_2])/([CO]+[CO_2])$ in the final syngas mixture to other values than about 3, depending on the intended subsequent use of the syngas.

Conversion of $CO_2$ to CO by a catalytic RWGS reaction has been recognized as a promising process for $CO_2$ utilization, and has been subject of numerous studies in the past decades. Early work proposed iron oxide/chromium oxide (chromite) as a suitable catalyst for this endothermic reaction; see e.g. U.S. Pat. No. 1,913,364. Disadvantages of this catalyst include methane formation.

In WO 96/06064 A1 a process for methanol production is described, which comprises a step of converting part of the carbon dioxide contained in a feed mixture with hydrogen to carbon monoxide, in the presence of a catalyst that is used conventionally for the WGS reaction; exemplified by a.o. a Zn—Cr/alumina catalyst.

GB 2279583 A discloses a catalyst for the reduction of carbon dioxide comprising at least one transition metal selected from Groups VIII and VIa, and teaches to use either ZnO alone, or on a composite material containing ZnO as support in order to increase selectivity and suppress methane formation.

The article by Ye et al. in Green Chemistry 2005, 7 524-528 relates to the effect that transition metal-modification of a chromia/alumina catalyst has on dehydrogenation of ethylbenzene to styrene, but it is also indicated that a 5% Ce-20% Cr/alumina catalyst shows activity in the reversed water gas shift reaction. This publication, however, does not address catalyst selectivity in reducing carbon dioxide with hydrogen into a syngas mixture, nor methane formation in said reaction.

A drawback of the known process as disclosed in US 2003/0113244 A1 is the selectivity of the catalyst employed; that is methane formation from carbon dioxide is still observed as a side-reaction. In the illustrative example this is quantified as 0.8 vol % of methane being formed in the gas output of the reactor, at a degree of conversion of carbon dioxide of 40%.

The object of the present invention is therefore to provide a catalyst that shows improved selectivity in reducing carbon dioxide with hydrogen into a syngas mixture, with only very little methane formation, and with good catalyst stability.

This object is achieved according to the invention by contacting a gaseous feed mixture containing carbon dioxide and hydrogen with a catalyst that substantially consists of chromium as active constituent, optionally at least one alkali metal or alkaline earth metal as promoter, and alumina as support.

With the process according to the present invention carbon dioxide can be hydrogenated into carbon monoxide with high selectivity, the catalyst showing good stability over time and under variations in processing conditions. Especially forming of methane, via a so-called methanation reaction is suppressed; typically only trace amounts of methane are found in the syngas mixture formed by the process according to the invention.

Methanation reactions are the reactions that produce methane and water from a carbon source, such as carbon dioxide and carbon monoxide, and hydrogen:

$$CO + 3H_2 \rightarrow CH_4 + H_2O$$

$$CO_2 + 4H_2 \rightarrow CH_4 + 2H_2O$$

In the process according to the present invention a product mixture is obtained containing an amount of formed methane of typically less than 0.5 vol %, preferably the amount of methane is less than 0.1 vol %, or even below the detection limit of CG equipment used for in-line analysis of the product stream. The process according to the invention thus shows very high selectivity towards syngas, more specifically to forming CO; CO selectivity is typically higher than 95%, preferably higher than 98%, and most preferably higher than 99% or even 99.5%.

The process of the invention shows good catalyst stability, also at temperatures of about 600° C. or above; meaning that the composition of the product mixture varies little over time.

A further advantage is that methane can be present in the feed mixture without affecting the reaction, and without being reacted itself; further demonstrating high selectivity of the catalyst used.

A further advantage of the process according to the invention is that the stoichiometric number (SN) of the syngas mixture obtained can be varied over a wide range, e.g. by varying the composition of the feed mixture. SN can, for example, vary from 0.5 to 3.0; making it possible to apply the syngas mixture obtained as a starting material in the synthesis of various other products; like alkanes, such as ethane, propane and iso-butane; aldehydes; ethers like dimethylether; or alcohols such as methanol. A further advantage is that the syngas made with the process of the invention can be applied without the need to separate excess $H_2$. Still a further advantage is that the process can be applied separately, but can also be combined with for example up-stream synthesis processes for a.o. above-mentioned products.

A special advantage of the present invention is that also spent chromia/alumina dehydrogenation catalyst, that is a catalyst that has been used in an alkane dehydrogenation process and which shows a significantly decreased dehydrogenation activity, can be applied with above-indicated advantages.

Within the context of the present application, a catalyst that substantially consists of chromium as active constituent, optionally at least one alkali metal or alkaline earth metal as promoter, and alumina as support is understood to mean that chromium (in the form of its oxides) forms the active sites of the catalyst composition, and that no other metals are added as active species. The catalyst contains alumina as its support material, and may further comprise an alkali or alkaline earth metal as promoter, and other inert components, like a binder material, or usual impurities, as known to the skilled person. Such catalyst containing only chromium as active constituent, alumina as support and optionally an alkali or alkaline earth metal as promoter will also be referred to herein as chromia/alumina catalyst.

The Cr-content of the catalyst may vary within broad ranges. A certain minimum content is needed to reach a desired level of catalyst activity, but a high content will increase the chance of particle (active site) agglomeration, and reduce efficiency of the catalyst. A suitable range is from 1 to 50 mass % (elemental Cr based on total mass of catalyst composition). Preferably, the catalyst contains from 5 to 30 mass % of chromium, more preferred ranges are from 8 to 25, or from 10 to 20 mass %.

Preferably, the catalyst used in the process according to the invention further comprises from 0.1 to 50 mass % (metal content based on total mass of catalyst composition) of at least one alkali or alkaline earth metal, because this further suppresses coke formation, and thus improves catalyst stability/life-time. More preferably, said metal is selected from the group consisting of Li, K, Cs and Sr. The advantage of such chromia/alumina catalysts comprising a promoter is that side-reactions in the process of the invention are even more effectively suppressed, especially methanation reactions. An additional advantage of these metals being present is that the catalyst is more robust, i.e. the support has better mechanical stability.

The amount of each alkali or alkaline earth metal component present in the catalyst used in the process according to the present invention may vary within indicated ranges; a preferred range is from 0.1 to 40 mass % (metal content based on total mass of catalyst composition). More preferably, said metal content is from 0.2 to 30 mass %, or even from 0.3 to 20 mass %.

The catalyst used in the process according to the invention contains alumina as carrier or support material. Without wishing to be bound to any theory, it is believed that chemical interactions between chromium and alumina lead to special structural properties (e.g. spinel type structures) that enhance catalytic performance in the targeted reaction. The surface area of the alumina appears not specifically critical in the present process. Preferably, the catalyst has a surface area of at least 50 $m^2/g$.

The catalyst composition according to the invention may further contain an inert binder or support material other than alumina, e.g. as a diluent. Suitable materials are known to the skilled person, and include for example silica or titanium oxides.

The catalyst that is used in the process of the invention may be prepared by any conventional catalyst synthesis method as known in the art. Generally such process includes the steps of making aqueous solutions of the desired metal components, for example from their nitrate or other soluble salt; mixing the solutions with alumina; forming a solid catalyst precursor by precipitation (or impregnation) followed by removing water and drying; and then calcining the precursor composition by a thermal treatment in the presence of oxygen.

The catalyst may be applied in the process of the invention in various geometric forms, for example as spherical pellets.

Preferably, the catalyst used in the process according to the invention is a chromia/alumina catalyst that has been used in an alkane dehydrogenation process, for example a propane or iso-butane dehydrogenation process. Such catalyst is referred to herein as spent dehydrogenation catalyst. Such spent catalyst is typically removed from a reactor, because the catalyst showed too low residual activity in said dehydrogenation process, most likely due to deactivation caused by coke formation, for continued use in said reactions. Coke deposition on the catalyst is generally thought to result in a change in physical properties of the catalyst particles, like a lower surface area and increased pore size; and the resulting decreased activity of the dehydrogenation catalyst cannot be increased again by a regeneration process. Regeneration with e.g. oxygen will remove coke, but will not restore the original structure. Such spent catalyst therefore has to be disposed of after its use in alkane dehydrogenation. It is therefore a great advantage and highly surprising that such spent dehydrogenation catalyst can be used in the process according to the invention, and that this process can be operated during prolonged times with good stability.

Preferably, the spent chromia/alumina dehydrogenation catalyst has been pre-treated with a gaseous mixture containing hydrogen at about 500-700° C. under atmospheric pressure during about 1 to 8 hours, before it is used as catalyst in the process according to the invention.

In the process according to the invention the step of contacting the gaseous feed mixture containing carbon dioxide and hydrogen with the catalyst can be performed over a wide temperature range. As the reaction is endothermic, a high temperature will promote conversion, but too high temperature may also induce unwanted reactions; therefore this step is preferably performed at a temperature of at least about 300° C., more preferably at least 400, 500, or even 550° C., but preferably at a temperature of at most about 900° C., more preferably at most 800° C., or even 750° C.

The step of contacting the gaseous feed mixture containing carbon dioxide and hydrogen with a catalyst according to the process of the invention can be performed over a wide pressure range. A higher pressure tends to enable lower reaction temperatures, but very high pressures are not practical. In addition, high pressure will increase methane formation;

therefore this step is preferably performed at a pressure above about atmospheric, but below 5 MPa, more preferably below 4 or 3 MPa, most preferably below 2 MPa.

The contact time in the step of contacting the gaseous feed mixture containing carbon dioxide and hydrogen with a catalyst according to the process of the invention may vary widely, but is preferably about from 0.5 to 6 s, more preferably from 1.5 to 5 s, or from 2 to 4 seconds.

The process according to the invention can be performed in conventional reactors and apparatuses; which are for example also used in methane reforming reactions. The skilled man will be able to select a suitable reactor set-up depending on specific conditions and circumstances. Suitable types of reactors include continuous fixed bed reactors. In view of the high reaction temperature, and catalytic activity of some metals like Ni in methanation reactions, use of a material comprising Ni or other active metals for making reactors walls etc. is preferably avoided. For this reason it is preferred to apply e.g. glass linings for relevant reactor parts.

In the process according to the present invention, carbon dioxide is selectively converted into carbon monoxide by a reverse water gas shift reaction in the presence of a chromia/alumina catalyst. The resulting product of this $CO_2$ hydrogenation process is a gas mixture containing carbon monoxide and water, and non-converted carbon dioxide and hydrogen. This reaction can, in case of excess hydrogen, also be represented by the following equation:

$$CO_2 + n\, H_2 \leftrightarrows CO + (n-1)H_2 + H_2O$$

The water formed in this reaction is generally removed from the product stream, because this will drive the equilibrium reaction in the desired direction, and because water is often interfering with subsequent reactions of the syngas. Water can be removed from the product stream with any suitable method known in the art, e.g. by condensation and liquid/gas separations.

The amount of hydrogen in the feed gas, that is the value for n in the above reaction scheme, may vary widely, for example from n=1 to n=5, to result in a syngas composition, e.g. expressed as its $H_2/CO$ ratio or as the stoichiometric number (SN), which can consequently vary within wide limits. The advantage thereof is that the syngas composition can be adjusted and controlled to match the desired use requirements.

Preferably, SN of the produced syngas mixture is from 0.1 to 3.0; more preferably SN is from 0.5 to 2.8 or even from 0.9 to 2.7. Such syngas product streams can be further employed as feed stock in different syngas conversion processes, such as oxygenates, especially methanol formation, olefin synthesis, reduction of iron oxide in steel production, or (hydro) carbonylation reactions.

In a preferred embodiment the feed gas contains equimolar amounts of $CO_2$ and $H_2$ (n=1 in above equation), resulting in a syngas composition that (at complete conversion and water removal) mainly consists of CO; which syngas is very suited for use in carbonylation reactions, for example carbonylation of methanol into acetic acid.

In another preferred embodiment, the feed gas contains $CO_2$ and $H_2$ in molar ratio of 1:2 (n=2 in above equation), resulting in a syngas composition with $H_2/CO$ or SN of about 1; which can be advantageously used for producing oxygenates, like dimethyl ether.

In a further preferred embodiment the feed gas contains $CO_2$ and $H_2$ in molar ratio of 1:3 (n=3 in above equation), resulting in a syngas composition with $H_2/CO$ or SN of about 2; which can be advantageously used in olefin or methanol synthesis processes.

The carbon dioxide in the gaseous feed mixture used in the process of the invention can originate from various sources. Preferably, the carbon dioxide comes from a waste or recycle gas stream, e.g. from a plant on the same site, like for example from ammonia synthesis, optionally with (non-catalytical) adjustment of the gas composition, or after recovering the carbon dioxide from a gas stream. Recycling such carbon dioxide as starting material in the process of the invention thus contributes to reducing the amount of carbon dioxide emitted to the atmosphere (from a chemical production site). The carbon dioxide used as feed may also at least partly have been removed from the effluent gas of the RWGS reaction itself.

The hydrogen in the feed may also originate from various sources, including streams coming from other chemical processes, like ethane cracking, methanol synthesis, or conversion of methane to aromatics.

The gaseous feed mixture comprising carbon dioxide and hydrogen used in the process of the invention may further contain other gases, provided that these do not negatively affect the reaction. Examples of such other gases include steam or methane. Methane is found not to be reactive in the process according to the invention; which means that a hydrogen stream containing methane, for example a recycle stream from another process, can be used to make the feed mixture. Preferably, the feed mixture contains at most about 20% of methane.

The feed may also contain oxygen, which does not negatively affect catalyst performance, although it is known that exothermic reactions initiated by oxygen under the applied reactions conditions may deteriorate catalyst activity.

The gaseous feed mixture preferably does not contain alkanes (except for methane), such as ethane, propane or iso-butane; because these compounds may lead to for example coke formation at the conditions applied.

The invention further relates to use of the syngas mixture obtained with the process according to the invention as feed material for a process of making a chemical product; like aliphatic oxygenates, especially methanol production, olefin synthesis (e.g. via Fischer-Tropsch reaction), aromatics production, carbonylation of methanol, carbonylation of olefins, or the reduction of iron oxide in steel production.

The invention therefore further relates to a process for making a chemical product using a syngas mixture as an intermediate or as feed material, which process comprises a step wherein carbon dioxide is hydrogenated according to the invention. Examples of such a process include production of aliphatic oxygenates, such as methanol, olefin synthesis, aromatics production, carbonylation of methanol, carbonylation of olefins, or reduction of iron oxide in steel production.

In a preferred embodiment, the invention concerns a process of making oxygenates via hydroformylation of olefins with syngas, comprising a step of carbon dioxide hydrogenation according to the invention, to result in a syngas mixture of suitable stoichiometry. The amount of CO formed in the RWGS step can also be controlled by the reaction temperature. Preferably, the syngas made has a composition characterized by a SN of about 1.

In another preferred embodiment, the invention concerns a process of making methanol via synthesis gas, comprising a step wherein carbon dioxide is hydrogenated according to the invention, to result in a syngas mixture of suitable stoichiometry; i.e. preferably having SN of about 2. For the step of making methanol from syngas in this process, any suitable synthesis process as known in the art can be applied. Preferably, in this process purge gas from the methanol synthesis reaction, containing hydrogen and carbon dioxide is recycled back to the carbon dioxide hydrogenation step. A further advantage of this process according to the invention is that the heat produced in the exothermic methanol synthesis step can be utilized in the endothermic RWGS step.

The invention will now be further elucidated with the following experiments.

EXAMPLE 1

A commercial chromia/alumina dehydrogenation catalyst, marketed by Süd-Chemie (DE) as Catofin® for dehydrogenation of propane or iso-butane, was applied as catalyst composition in this experiment. This catalyst contains about 13 mass % of Cr.

A glass tube was filled with about 6 ml of fresh catalyst to make a fixed bed type of reactor, and was placed vertically inside a temperature controlled oven. First hydrogen was passed over the catalyst particles at 600° C., during 2 hours, then a gaseous feed mixture was made by mixing carbon dioxide and hydrogen, and was passed through the reactor tube with an inlet flow rate of 52 ml/min (controlled with a mass flow controller). The composition of the resulting syngas mixture (product) was measured in-line with gas chromatography, after removing water from the mixture in a cold trap. The reaction was performed at atmospheric pressure, other conditions and results are presented in Table 1. In the syngas mixture the amount of methane was too low to be reliably quantified; meaning the concentration was below 0.1 vol %, and CO selectivity over 99.5%.

TABLE 1

| Conditions | | | | |
|---|---|---|---|---|
| Temperature | Time of reaction | Gas composition (vol %) | | |
| (° C.) | (months) | $CO_2$ | $H_2$ | CO |
| | 0 - Feed | 25.0 | 75.0 | 0 |
| 600 | 1 | 11.8 | 69.9 | 17.9 |
| 600 | 2 | 11.1 | 72.3 | 16.6 |

EXAMPLE 2

The same chromia/alumina catalyst of Example 1, but now material that was removed from a propane dehydrogenation reactor because its activity had dropped to below a certain minimum, was used as catalyst (spent dehydrogenation catalyst). The experiments were performed analogous to Example 1, but a tube filled with 3 gram of catalyst was applied. The spent catalyst was first treated with hydrogen at 600° C. during 2 hours, after which the feed was changed to a hydrogen/carbon dioxide mixture. The results as presented in Table 2 indicate this spent catalyst still shows favourable activity in the RWGS reaction, and is not affected by presence of oxygen.

The BET surface area of spent catalyst was measured as 60 g/m², versus 90 g/m² for the fresh catalyst. Pore sizes for spent and fresh chromia/alumina catalyst were found to be about 76 and 45 Å, respectively, indicating structural changes in the catalyst after its use in propane dehydrogenation.

EXAMPLE 3

Experiments were performed analogously to Example 2, but a glass tube filled with about 6 ml of spent catalyst was used. Results collected in Table 3 indicate that stable syngas production occurs during 5 months. No methane could be detected.

EXAMPLE 4

In this experiment the gas feed mixture contained also methane, further it was performed as Example 3; results are presented in Table 4.

TABLE 2

| Conditions | | | | |
|---|---|---|---|---|
| Temperature | Time of reaction | Gas composition (vol %) | | |
| (° C.) | (hours) | $CO_2$ | $H_2$ | CO |
| | 0 - Feed | 23.5 | 76.5 | 0 |
| 540 | 1 | 13.1 | 75.6 | 11.2 |
| 540 | 2 (After 20 min. air flow) | 12.6 | 76.0 | 11.2 |
| 540 | 168 | 13.8 | 73.8 | 12.3 |
| 550 | 1480 | 15.7 | 74.6 | 9.5 |

TABLE 3

| Conditions | | | | |
|---|---|---|---|---|
| Temperature | Time of reaction | Gas composition (vol %) | | |
| (° C.) | (months) | $CO_2$ | $H_2$ | CO |
| | 0 - Feed | 25.6 | 74.4 | 0 |
| 600 | 1 | 12.2 | 70.2 | 17.6 |
| 600 | 2 | 12.6 | 69.9 | 17.4 |
| 600 | 3 | 11.8 | 70.9 | 17.2 |
| 600 | 4 | 12.8 | 68.5 | 18.6 |
| 600 | 5 | 11.0 | 71.4 | 17.6 |

TABLE 4

| Conditions | | | | | |
|---|---|---|---|---|---|
| Temperature | Time of reaction | Gas composition (vol %) | | | |
| (° C.) | (months) | $CO_2$ | $H_2$ | CO | $CH_4$ |
| | 0 - Feed | 26.6 | 62.7 | 0 | 10.1 |
| 600 | 1 | 10.9 | 62.2 | 16.2 | 10.6 |
| 600 | 2 | 11.4 | 60.0 | 16.9 | 11.5 |

EXAMPLE 5

Experiments were performed analogously to Example 3, but performed on bench scale with a catalyst loading of 100 ml, and gas inlet flow rate of 625 ml/min. Results collected in Table 5 indicate that stable syngas production occurs during 3 months, without methane being detected.

TABLE 5

| Conditions | | | | |
|---|---|---|---|---|
| Temperature | Time of reaction | Gas composition (vol %) | | |
| (° C.) | (months) | $CO_2$ | $H_2$ | CO |
| | 0 - Feed | 18.6 | 81.4 | 0 |
| 596 | 1 | 8.3 | 77.6 | 15.2 |
| 600 | 2 | 7.1 | 78.4 | 15.0 |
| 600 | 3 | 7.9 | 76.2 | 15.9 |

The invention claimed is:

1. A process of making a syngas mixture containing hydrogen, carbon monoxide and carbon dioxide, comprising a step of contacting a gaseous feed mixture containing carbon dioxide and hydrogen with a catalyst, consisting essentially of chromium as active substituent, optionally at least one alkali metal or alkaline earth metal as promoter, and alumina as support.

2. The process according to claim 1, wherein the catalyst contains from 5 to 30 mass % of chromium.

3. The process according to claim 1, wherein the catalyst comprises from 0.2 to 30 mass % of at least one member selected from the group consisting of Li, K, Cs and Sr.

4. The process according to claim 1, wherein the catalyst is a spent chromia/alumina dehydrogenation catalyst.

5. The process according to claim 4, wherein the spent catalyst has been pre-treated with a gaseous mixture containing hydrogen at about 500-700° C. under atmospheric pressure during 1-8 hours.

6. The process according to claim 1, wherein the contacting step is carried out at a temperature of from 300 to 900° C., at a pressure of from 0.1 to 5 MPa, and with a contact time of from 0.5 to 6 s.

7. The process according to claim 1, wherein the feed mixture contains hydrogen and carbon dioxide in a ratio of from 1 to 5.

8. The process according to claim 1, wherein the syngas has a stoichiometric number of from 0.1 to 3.0.

9. The process according to claim 1, wherein the feed mixture further comprises methane.

10. A process for making a chemical product using a syngas mixture as an intermediate or as feed material comprising a step of contacting a gaseous feed mixture containing carbon dioxide and hydrogen with a catalyst consisting of chromium as active substituent, optionally at least one alkali metal or alkaline earth metal as promoter, and alumina as support.

* * * * *